United States Patent [19]

Cho

[11] Patent Number: 4,815,116

[45] Date of Patent: Mar. 21, 1989

[54] METHOD AND APPARATUS FOR X-RAY ANALYSIS OF RAPIDLY MOVING MULTICOMPONENT MATERIALS

[75] Inventor: Boong Y. Cho, Columbus, Ohio

[73] Assignee: Process Automation Business, Inc., Columbus, Ohio

[21] Appl. No.: 302,959

[22] Filed: Sep. 17, 1981

[51] Int. Cl.$^4$ .................... G01N 23/06; G01N 23/16
[52] U.S. Cl. ............................. 378/53; 378/45
[58] Field of Search ..................... 378/51, 53, 45

[56] References Cited

U.S. PATENT DOCUMENTS

| Re. 30,884 | 3/1982 | Buchnea .................. 378/53 |
| 2,445,305 | 7/1948 | Hochgesang . |
| 2,983,819 | 5/1961 | Bigelow . |
| 3,030,512 | 4/1962 | Harker ..................... 378/45 |
| 3,100,261 | 8/1963 | Bigelow .................... 378/53 |
| 3,114,832 | 12/1963 | Alvarez . |
| 3,121,166 | 2/1964 | Vossberg . |
| 3,287,560 | 11/1966 | Morgan . |
| 3,366,790 | 1/1968 | Zagorites . |
| 3,412,249 | 11/1968 | Hanken . |
| 3,417,244 | 12/1968 | Kramer . |
| 3,435,220 | 3/1969 | Hanken ..................... 378/53 |
| 3,525,863 | 8/1970 | Constantine et al. ........ 378/45 |
| 3,581,087 | 5/1971 | Brinkerhoff ............... 378/45 |
| 3,701,899 | 10/1972 | Voparil . |
| 3,843,884 | 10/1974 | Evans . |
| 3,904,876 | 9/1975 | Arendt ..................... 378/53 |
| 4,081,676 | 3/1978 | Buchnea . |
| 4,090,074 | 5/1978 | Watt . |
| 4,168,431 | 9/1979 | Henriksen ................. 378/53 |

FOREIGN PATENT DOCUMENTS

| 48-16877 | 5/1973 | Japan ..................... 378/53 |
| 55-94149 | 7/1980 | Japan ..................... 378/53 |
| 958240 | 5/1964 | United Kingdom . |

OTHER PUBLICATIONS

Kirkpatrick, Paul, "On the Theory and Use of Ross Filters," *Review of Scientific Instruments,* vol. 10, pp. 186–191 (1939).

Cho, B. Y. and Utt, O. L., "A New TiO$_2$ Compensated X-Ray Ash Sensor for Paper", a preprint No. 75-611 of a paper presented at the Instrument Society of America, Industry Oriented Conference and Exhibit, Milwaukee, Wisc. Oct. 6–9, 1975.

Utt, O. L. and Cho, B. Y., "Composition Compensated Paper Ash Gauge", a preprint of a paper presented at the ERDA Symposium on X- and Gamma-Ray Sources and Applications, Ann Arbor, Mich., May 19–21, 1976.

*Primary Examiner*—Craig E. Church
*Assistant Examiner*—T. N. Grigsby
*Attorney, Agent, or Firm*—Richard H. Berneike

[57] ABSTRACT

A beam of X rays is directed into a traveling product such as paper having a constituent such as ash made up of components such as clay, chalk and titanium dioxide.

X rays from the product may produce signal channel responses that are the same to one component but different to another component, and a resultant response indicative of the content of the constituent or component.

The X rays from the product may produce a response to a detected spectrum wherein the intensities of the rays are so distributed as a function of energy that the average effective absorption coefficients for the components are substantially equalized, so that the response will be indicative of the constituent and comparatively unaffected by the relative amounts of the components.

32 Claims, 2 Drawing Sheets

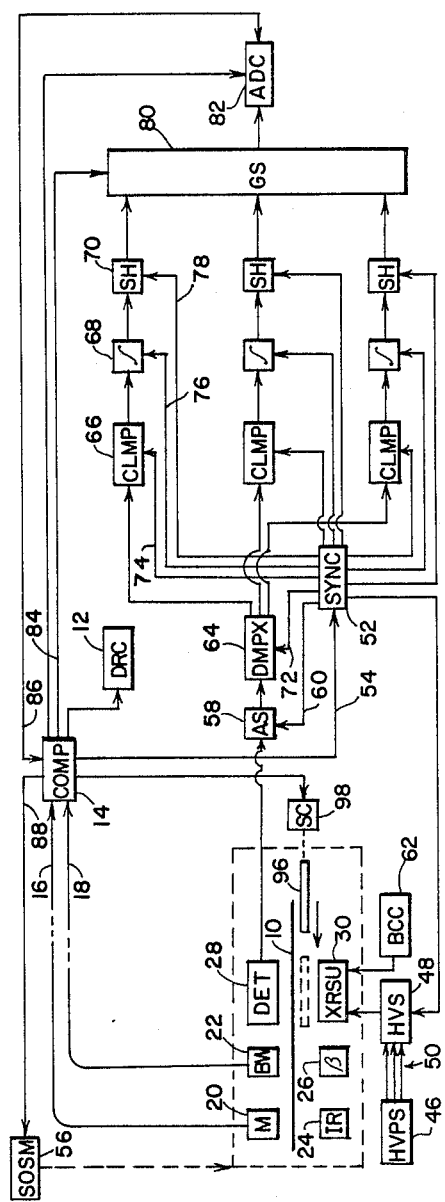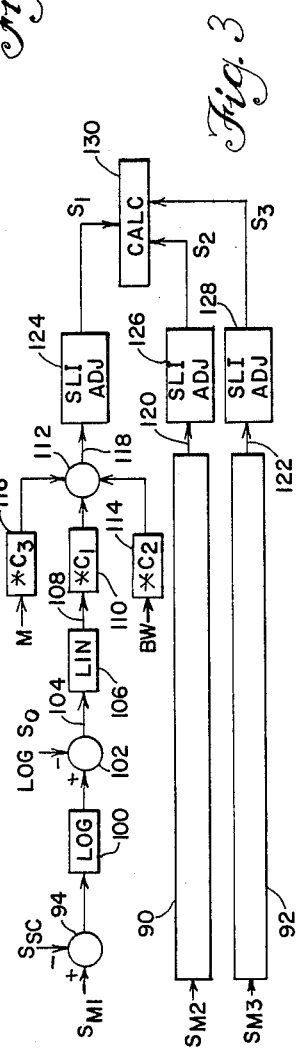

METHOD AND APPARATUS FOR X-RAY ANALYSIS OF RAPIDLY MOVING MULTICOMPONENT MATERIALS

TECHNICAL FIELD

This invention relates to methods and apparatus for x-ray analysis of multicomponent materials, especially fast traveling materials that are continuously formed in a manufacturing process. More particularly, in one aspect, the invention relates to methods and apparatus whereby analyzing rays from the material can be made to produce, in separate channels, normalized channel responses that are substantially the same to one component but different to other components, thus enabling computation of a relatively clear, unambiguous and relatively high speed response indicative of the content of a constituent or component in the material.

While the invention has many possible applications, it is herein shown and described in an embodiment for non-destructively analyzing fast-traveling paper sheets for ash content and ash components.

In another aspect, the invention relates to a method and apparatus for measuring the amount of the ashforming constituent in paper using an x-ray spectrum so shaped that the measurement is comparatively unaffected by the relative amounts of clay, chalk and titanium dioxide that make up the ash constituent. The method and apparatus can also be generalized to other products wherein the measurement of a constituent is possible according to the invention where the nature of the material permits.

BACKGROUND ART

There have been many proposals and developments for analyzing materials by absorption edge analysis such as K-edge analysis. Pertinent examples are found in the U.S. Pat. Nos. 3,100,261 Bigelow, 3,114,832 Alvarez and 3,701,899 Voparil.

U.S. Pat. Nos. 3,904,876 Arendt and 4,081,676 Buchnea set out two proposals for commercial multicomponent paper ash analyzers, while U.S. Pat. No. 4,090,074 Watt contains a proposal for determining coal ash content and ash components.

Two articles by Cho, B. Y. and Utt, O. L., "A New TiO$_2$ Compensated X-Ray Ash Sensor for Paper," a preprint No. 75-611 of a paper presented at the Instrument Society of America, Industry Oriented Conference and Exhibit, Milwaukee, Wis., Oct. 6-9, 1975, and "Composition Compensated Paper Ash Gauge," a preprint of a paper presented at the ERDA Symposium on X- and Gamma-Ray Sources and Applications, Ann Arbor, Mich., May 19-21, 1976, describe a single-channel x-ray gauge, for paper, that measures the total ash content in binary ash-forming mixtures such as titanium dioxide and calcium carbonate, calcium carbonate and clay, or clay and commercial success, it is frequently desired to be able to separately measure the individual components of the ash forming constituent in the paper. For example, if the ash constituent consists of clay and titanium dioxide, since the titanium dioxide is a much more expensive ingredient than the clay, it may be desired to continuously determine, from measurements of the traveling paper sheet per se, what fraction or percentage of the paper or ash forming material weight is titanium dioxide and/or what percentage or fraction is clay. It is also desired to be able to measure the total ash content of paper wherein the ash forming constituent is a tertiary mixture of clay, calcium carbonate and titanium dioxide, for example, or perhaps the content of one or more of these individual components in the paper may be of interest.

In laboratories, discrete static samples of material are commonly analyzed by taking several measurements with different wavelengths of well-monochromatized radiation. Fluorescent radiators and/or diffractometers, as well as certain radioisotope sources may be used to obtain the effectively monoichromatic rays that may be initially directed into the sample, and diffractometers and/or energy selective detection apparatus, possibly using a multichannel analyzer, may be used to evaluate the intensity of different wavelengths received from the sample. Digital computers facilitate the mathematical process of converting the signal intensity information to quantitative valves indicative of the content of various components in the sample.

Since relatively fast and powerful digital computers have come into common use as an aid to the measurement and control of continuous industrial processes such as paper manufacture, there have been proposals to adapt these and similar laboratory techniques to the analysis of multicomponent materials during production. In a complex problem such as paper ash component analysis, the mathematical equations are frequently unsolvable, but solutions may be theoretically possible using iterative computations. Hence in some theoretical discussions of these proposals it is sometimes implied that ash component analysis, for example, can be usefully performed on line during the paper making process. As a matter of fact, however, with the practical radiation intensity limitations on usable sources and detectors, there simply is not sufficient integration time available on line to obtain reliable ash component analyses using these adaptations of the laboratory methods. They are thus generally limited in practical application to the measurement of total ash in a binary ash constituent mixture, a task which the apparatus of Utt and Cho, supra, has been able to perform in a much simpler and more reliable manner.

DISCLOSURE OF INVENTION

According to the invention, there are provided combinations of method steps and means adapted for determining a constituent or component of a traveling product that is continuously formed from materials having components of different atomic numbers, comprising directing into the product a beam of x rays having energies including an absorption edge energy for at least one of the components, receiving x rays from the product and responding to the received rays to produce a first channel response and a second channel response, the two channel responses being responsive to two different energy spectra in a manner such that the channel responses are substantially the same to one component and different to the other component, and responding to the first and second channel responses to produce a resultant response indicative of the content of the constituent or component in the product.

Typically, at least one of the two channel responses is normalized so that after the normalization both channel responses are substantially the same to one component although different to the other component.

At least one of the energy spectra may be selected to make the response of the one channel to the other component substantially the same as its response to the one component.

Typically the method may comprise shifting the x-ray energies in the beam, in a repeating sequence between a first energy spectrum and a second energy spectrum, and responding to the first and second energy spectra sequentially to produce the first and second channel responses. At least one of the energy spectra may be selected so as to make the response of the one channel to the other component substantially the same as it is to the one component.

The energy shifting sequence may include a third energy spectrum, and a third channel response may be produced by responding to the third energy spectrum. At least one of the energy spectra may be selected so as to make the response of the one channel to the other component substantially the same as it is to the one component, and another of the energy spectra may be selected so as to make the response of the third channel substantially the same to a third component as it is to either the one component or to the other component. The x-ray energies in the beam may be shifted by applying different high voltages sequentially to an x-ray tube.

The x rays from the product may be received with a first detector that detects a portion of the received rays to originate the first channel response and transmits a second portion of the received rays, and the rays transmitted by the first detector may be detected to originate the second channel response. The rays transmitted by the first detector may be filtered to reshape their energy spectrum before they are detected to originate the second channel response. The filtering may be such as to selectively reduce the relative intensity of those rays having energies above the absorption edge energy for the one component.

The rays from the product may be filtered before they are received by the first detector to selectively reduce the relative intensity of those rays having energies below the absorption edge energy for the one component but above the absorption edge energy for the other component. In this case also the rays transmitted by the first detector may be filtered to further reshape their energy spectrum before they are detected to originate the second channel response.

Typically the product is paper being manufactured by a paper making machine and the constituent is the ash-forming material in the paper, the paper having a variable basis weight and a variable moisture content, and method steps and apparatus are provided for detecting the received rays to produce a first and a second originating response, producing responses to the basis weight and moisture content of the paper, compensating each of the first and second originating responses according to the basis weight and moisture content responses, and deriving the first and second channel responses from the compensated responses so that the channel responses are functions of the ash constituent and substantially independent of the basis weight and moisture contents of the paper. The ash constituent may have at least two components, and at least one of the first and second channel responses may be normalized so that after the normalization both responses are substantially the same to one ash component although different to the other component. At least one of the energy spectra may be selected to make the response of the one channel to the other ash component substantially the same as its response to the one ash component.

In accordance with another aspect of the invention, there is provided a method and apparatus for measuring a traveling sheet of paper or the like exhibiting variations in the vicinity of a nominal basis weight and a nominal composition including an ash-forming constituent made up of any or all of the components of clay, chalk and titanium dioxide, comprising the steps of, and apparatus for directing into the paper a beam of x rays having energies including the K-edge energy for titanium, receiving x rays from the paper and producing a response to a spectrum of the received rays wherein their intensities are so distributed as a function of energy that the average effective absorption coefficients for the clay, the chalk and the titanium dioxide are substantially equalized for the nominal basis weight and composition of the paper, the response being indicative of the amount of the ash-forming constituent in the paper and comparatively unaffected by the relative amounts of the clay, chalk and titanium dioxide therein.

The beam of x rays directed into the paper may be produced by an x-ray source unit including an x-ray tube energized at around 5½ kilovolts. The spectrum may be formed by passing the x rays through a filter that selectively absorbs rays having energies between the Kedge energies for calcium and titanium. The filter may comprise a weight per unit area of tin equivalent to a tin thickness of about for to eight micrometers.

In one generalized aspect, the invention provides a method and apparatus for measuring a traveling product exhibiting variations in th vicinity of a nominal mass per unit area, length or volume, and in the vicinity of a nominal composition including a constituent of interest made up of any or all of three components respectively formed from distinctive chemical elements, at least two of which have absorption edges in neighboring regions of the x-ray spectrum, comprising the steps of, and apparatus for, directing into the product a beam of x rays having energies including the highest significant absorption edge energy for the respective elements of the components, and receiving x rays from the product and producing a response to a detected spectrum of the received rays wherein their intensities are so distributed as a function of energy that the average effective absorption coefficients for the three components are substantially equalized for the nominal mass per unit area, length or volume and the nominal composition of the product, the response being indicative of the amount of the constituent of interest in the product and comparatively unaffected by the relative amounts of the three components therein.

The objects of the invention are to provide improved x-ray methods and apparatus for analyzing or measuring a constituent such as multicomponent ash in a traveling multiconstituent material such as paper; which methods and apparatus can utilize relatively broad x-ray spectra for producing its responses; which can utilize one or more stable, relatively non-energy-selective, high intensity radiation detectors such as ionization chambers; which can accordingly provide higher signal to noise ratios and faster response with an industrially practical radiation source, which can determine the total amount of a tertiary constituent with essentially a single measurement, without the necessity for measuring the components separately and adding them, thus avoiding the additive errors, and wherein the analysis involves mathematical equations that admit of direct and simple solutions, thus producing substantial savings in computer time.

Other objects and advantages will become apparent in the following detailed description, taken in conjunction with the appended drawings.

BRIEF DESCRIPTION OF THE DRAWINGS

FIG. 1 is a block diagram showing the interrelation of apparatus elements used to acquire the data for analyzing a multicomponent ash-forming constituent in a traveling paper sheet such as one being formed continuously by a paper making machine, in accordance with one embodiment of the invention.

FIG. 3 is a diagram showing the nature and sequence of mathematical operations performed using data acquired by apparatus such as that of FIG. 1 or FIG. 4.

MODES FOR CARRYING OUT THE INVENTION

Figure 2:
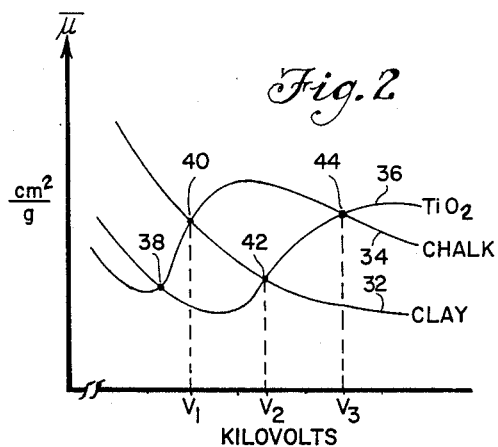
FIG. 2 is a graph showing average effective x-ray absorption coefficients for clay, chalk and titanium dioxide as a function of voltage applied to an x-ray tube.

Referring to FIG. 1, the numeral 10 designates a continuously formed sheet of paper that may be visualized to be moving in the direction of the observer. Typically the sheet 10 would be traveling from the calender stack to the windup section of a paper making machine (not shown). The purpose of the diagrammatically represented apparatus is to operate suitable display, recording and control devices 12 that are conventionally under the control of a digital computer 14.

Via lines 16 and 18, the computer 14 receives moisture content and basis weight information from a moisture detector 20 and a basis weight detector 22. The moisture detector 20 responds to infrared radiations, transmitted through the sheet 10, from a source 24, and the basis weight detector 22 responds to beta radiation from a source 26. A further detector 28 is provided to enable the ash forming constituent of the paper 10 to be measured, either as total ash or as individual ash components.

Detector 28 responds to low-energy x rays, transmitted through the sheet 10, from an x-ray source unit 30 containing a suitable x-ray tube. Typically the moisture detector 20 is a suitable solid state photodetector, while detectors 22 and 28 are ionization chambers, each of a suitable design. In response to the information received from the detectors, the computer 14 activates the display, recording and control devices 12 in accordance with programmed instructions and inputs from the machine operators. Basis weight, moisture content and other computed data may be displayed and/or recorded, and the adjustable operating parameters of the paper making machine may be automatically controlled to maintain various properties of the sheet 10 substantially constant at desired values.

The illustrated embodiments of the present invention are arranged particularly to provide the system with the capability of measuring and/or controlling the content and/or composition of the ash forming constituent of the paper 10. Ordinarily the other two principal consituents are cellulose fiber and water (the moisture content). The ash-forming constituent generally includes clay as an inexpesive filler, together with either titanium dioxide, ($TiO_2$) or chalk, or possibly both, as a whitener.

To distinguish the ash forming constituent from the other constituents in the paper, the x-ray system 28 and 30 relies heavily on the presence of the atoms of aluminum and silicon in clay, the atoms of titanium in $TiO_2$ and the atoms of calcium in chalk. To distinguish between the components of the ash forming constituent, the system relies on the presence of the titanium K-edge at 4.966 kev and the calcium K-edge at 4.037 kev.

FIG. 2 is a plot of the average effective attenuation coefficients $\bar{\mu}$ for clay at 32, chalk at 34 and $TiO_2$ at 36, as a function of the x-ray tube high voltage. The rays from the x-ray source unit 30 are not monochromatic or monochromatized, but constitute a relatively broad spectrum. Hence the average effective attentuation coefficients $\bar{\mu}$ do not exhibit sudden step changes in value as a result of the K-edges, although the K-edge absorption processes do produce the crossover points at 38, 40, 42 and 44. The ash gauge of Utt and Cho supra has taken advantage of these crossover points to measure the amount of the ash forming constituent in paper where this constituent has consisted of a binary mixture.

It was found, for example, that all clays used in the paper making processes investigated have about the same $\bar{\mu}$ values regardless of their geographic origin. Most paper making processes in the United States use a mixture of clay and $TiO_2$, whereas most paper making processes in Europe use a mixture of clay and chalk.

With an anode voltage setting of $V_2$, the gauge will measure the total amount of the paper ash forming constituent regardless of the relative amounts of the clay and $TiO_2$ components in the binary mixture. Similarly the total ash constituent in paper containing a binary mixture of clay and chalk can be measured with an anode voltage setting of $V_1$. With the x-ray tube, source and detector windows and other geometric arrangements used in the gauge of Utt and Cho supra, $V_1$ was 4.2 kev and $V_2$ was 5.3 kev, thus placing the proper percentages of the respective integrated x-ray spectra above and below the respective clay or titanium K-edges. With the appropriate one of these settings, the gauge responds in exactly the same way to clay and $TiO_2$ or clay and chalk.

The FIG. 1 embodiment of the present invention utilizes an extension of the foregoing principle. Here a high voltage power supply unit 46 is adapted to supply any one of two, or three, or possibly more predetermined voltages to the x-ray source unit 30 in accordance with the selected state of an associated high voltage switching unit 48. As illustrated in FIG. 1, it is indicated that there are three available voltages, represented visually by three lines in the group shown at 50. These voltages correspond to $V_1$, $V_2$ and $V_3$ of FIG. 2. $V_3$ corresponds also to the crossover point 44 where the x-ray gauge 28 and 30 produces substantially the same response to chalk that it does to $TiO_2$. The crossover point 44 is used instead of point 38 because a higher detector signal level can be achieved and more high voltage variation can be tolerated.

During normal measurement the voltages $V_1$, $V_2$ and $V_3$ are successively applied in a repetitive, periodic sequence to the x-ray source unit 30. This causes the x-ray energies in the beam from x-ray source unit 30 to be shifted in a repeating sequence between a first, a second and a third energy spectrum. The switching is performed by the high voltage switching unit 48 under control of a conventionally designed synchronizer unit 52. As visually indicated by a line 54, the synchronizer 52 is in turn under the control of the computer 14 so that the voltage switching operations will occur at points in time that are compatible with data sampling operations and the placement of data in certain computer "memory slots" or "data boxes". These operations in turn may need to be correlated with the instantaneous position of the sensors across the width of the sheet 10 as determined by a scanning and off sheet mechanism 56 that is also under the control of the computer 14. While deserving mention herein, the synchronizing details are of a conventional nature and form no part of the present invention.

The output of the x-ray detector 28 is amplified by an amplifier system 58. Due to the fact that the high voltage to the x-ray source unit is being changed substantially and periodically, there may be a very wide dynamic range of signal output currents from the ionization chamber (detector) 28. It may thus be appropriate to use a gain-switched amplifier system 58 controlled by the synchronizer 52 as visually suggested by a line 60. As a way of reducing the dynamic range required of the amplifier system 58 and other components the x-ray source unit 30 may be provided with an x-ray tube beam current control device 62.

Either the amplifier gain switching arrangement, the beam current control system or both may be appropriately used depending on the application. It should be noted that in addition to the measurement of ash forming materials incorporated in various weights of paper to increase opacity and brightness, the methods and apparatus of the invention may be used to measure constituents and components of other materials, such as paper coated with zinc oxide or selenium compounds. Other uses may include measuring the chlorine content or plastics or the ferric oxide coatings on tapes.

The signal from detector 28, after amplification by amplifier system 58, is demultiplexed into two or three (as shown) separate channels by a demultiplexer 64, whose switching operations are controlled by the synchronizer 52. As shown, the first channel includes a switched clamp circuit 66, an integrator 68 and a sample and hold circuit 70. The operation of these elements is controlled by the synchronizer, as visually suggested by lines 72, 74, 76 and 78. The other two channels contain identical elements. The signal provided by the sampling and hold circuits as at 70 are available to the computer 14 for sampling in numerical form by operation of a gating system 80 and an analog to digital converter 82. By controlling the gating system 80 and converter 82 as visually suggested by lines 84 and 86 the computer 14 collects the data at appropriate times as indicated by line 88 and commits it to memory for use in computations as outlined in FIG. 3.

As shown in FIG. 3, the computer maintains the separate channel identity of the data received. Thus $S_{M1}$ designates values or originating responses in the first channel corresponding to values of the signal output from detector 28 in response to x rays transmitted through the paper 10 when the x-ray source unit 30 is energized with the high voltage designated as $V_1$ in FIG. 2. Similarly $S_{M2}$ and $S_{M3}$ respectively designate values in the second and third channels 90 and 92 corresponding in the same manner to high voltages $V_2$ and $V_3$ respectively. The computations performed on the second and third channel data are identical to those illustrated for the first channel and are described as follows.

At 94 each $S_{M1}$ value has subtracted therefrom a value $S_{SC}$. $S_{SC}$ is a previously stored standardization value that represents the signal output of the detector 28 with x-ray source unit 30 energized with voltage $V_1$ and with a thick shutter 96 (FIG. 1) between the x-ray source unit 30 and the position of paper 10. The shutter is operated at appropriate times by a shutter control unit 98 that is in turn under control of the computer 14. Thus $S_{SC}$ represents the signal output of detector 28 when an "infinitely" thick sheet of paper is between the detector and the x-ray source unit 30.

A logarithm of the remaining $S_{M1}$ value is taken at 100. Log $S_o$ is subtracted at 102. $S_o$ represents a previously stored standardization value of the output of detector 28 with the shutter 96 open and with the detector in an off sheet position or under other conditions where there is no paper sheet 10 between the detector 28 and the x-ray source unit 30, which is energized with the high voltage $V_1$. Conventionally, the computer 14 obtains an updated log $S_o$ value periodically or at convenient times by operating the scanning and off sheet mechanism 56 to move the sensors (20 and 24), (22 and 26) and (28 and 30) to the off sheet position for standardization. The value obtained at 104 thus represents the ratio of the detector 28 output with the paper 10 in the gap to the detector output with the paper 10 absent.

The value 104 is adjusted if necessary at 106 to place it in a linear continuum of values determined by a function such as $$y = \frac{x}{a + bx + cx^2 + dx^3} \quad (1)$$

where x represents the value at 104 and y represents the value at 108. The linearizing constants a, b, c and d are determined in a calibration step using samples of a suitable sheet material such as the polyester resin that is marketed under the trademark Mylar. These samples have a range of weight per unit area values and are placed successively in the position occupied by the paper 10 during its measurement. The values of the linearizing constants are determined so as to make the values obtaining at 108 a linear function of of the weight per unit area of the polyester sheet material.

The values at 108 are multiplied at 110 if necessary by a suitable scaling constant $C_1$, and the resulting values are summed at 112 with linearized and scaled values representing the moisture content M and basis weight (weight per unit area) BW of the paper. In FIG. 3, M represents an input of linearized values for the moisture content as detected with the infrared moisture gauge head at 20, 24. Similarly BW represents an input of linearized values of the basis weight as detected with the beta ray gauge head 22, 26. Thus each BW value is multiplied at 114 by a scaling constant $C_2$ and each M value is multiplied at 116 by a scaling constant $C_3$.

The values for the constants $C_1$, $C_2$ and $C_3$ are determined in calibration, using actual samples of paper 10 containing the appropriate ash forming constituent and having a range of basis weight and moisture values. For calibrating the first channel, one uses appropriate paper samples containing an ash forming constituent of clay or chalk or both, and the constants are determined so that the resultant values at 118 are not substantially affected by changes in M or BW but do respond appropriately to changes in the amount of the ash constituent. At this point also tests are made, for example, using samples containing only clay and samples containing only chalk as an ash constituent to ensure that the channel does indeed respond in substantially the same manner to the chalk component as it does to the clay component. If not, the high voltage $V_1$ must be readjusted since it is not accurately aligning the x-ray spectrum to achieve operation at the crossover point 40 (FIG. 2).

The other channel or channels 90 and 92 operate and are calibrated in a similar manner, using paper samples containing clay and $TiO_2$ for calibration of channel 90 and samples containing chalk and $TiO_2$ for calibration of channel 92.

The values obtained in the first channel at 118, in the second channel at 120 and in the third channel at 122 are subsequently normalized so that all three channels respond in exactly the same manner to the clay component of ash. To this end, at least two of the values at 118, 120 and 122 are subjected to a slope-intercept adjustment as indicated at 124, 126 and 128. This simply consists in multiplying the successive values obtained at 118, for example, by an appropriate slope adjustment factor S and adding an intercept adjustment constant I in accordance with $$y = Sx + I \quad (2)$$

where x is the value obtained at 118, 120 or 122 and S and I are selected appropriately so that $$y_{118} = y_{120} = y_{122} \quad (3)$$

when paper samples with an ash constituent containing only clay are measured with the instrument.

In FIG. 3 the normalized first channel response is identified as $S_1$; the normalized second channel response is identified as $S_2$ and the normalized third channel response is identified as $S_3$. These responses are constitued as $$S_1 = C + AT + H \quad (4)$$

$$S_2 = C + T + \beta H \quad (5)$$

$$S_3 = C + \delta(T + H) \quad (6)$$

where C represents the clay content of the paper, T represents the $TiO_2$ content and H represents the chalk content. A, $\beta$ and $\delta$ are constants.

Considering Equation (4), for example, in view of FIG. 2, by choosing voltage $V_1$ and the crossover point 40, the x-ray energy spectrum has been selected to make the clay and the chalk produce equal responses that can be considered unitary because of the normalization. However, $TiO_2$ affects the signal only about half as much as the clay or the chalk and hence the value of A is close to ½. Considering Equation (5), at voltage $V_2$ clay and $TiO_2$ produce equal and unitary (because of the normalization) responses, but chalk affects the signal about 1.6 times as much, and hence the value of $\beta$ is close to 1.6. At $V_3$ the response to clay is unitary because of the normalization, but either $TiO_2$ or chalk affects the signal about twice as much, and hence the value of $\delta$ is close to 2.0. Exact values for A, $\beta$ and $\delta$ can be determined in calibration for each individual gauge, and the calculation required to solve equations (4), (5) and (6) as indicated at 130 for any or all of the C, T and H components, and/or the total ash constituent in the paper 10 is a trivial matter.

Figure 4:
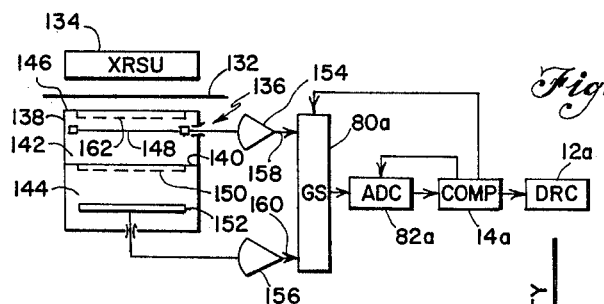
FIG. 4 is a diagram of an arrangement using "double-deck" ionization chamber detectors for acquiring ash component data to be used for the computations of FIG. 3, according to another embodiment of the invention.

In other modes for carrying out the invention, instead of using the high voltage switching arrangement of FIG. 1 the components of a binary ash constituent in paper or the total ash constituent of a tertiary ash forming mixture in paper, for example, can be measured using a double-deck detector arrangement as illustrated diagrammatically in FIG. 4.

Here the paper sheet 132 passes continuously between an x-ray source unit 134 and a double-deck detector 136. During measurement, the high voltage supplied to the x-ray source unit 134 is highly stabilized and constant to produce a beam of x-rays having a predetermined energy spectrum and a constant output intensity. As in the FIG. 1 embodiment, the spectrum includes an absorption edge energy for at least one of the ash components. As in FIG. 1, the source unit 134 directs the beam of x rays into the traveling paper sheet product 132, and the double-deck detector arrangement 136 receives from the product the rays that are transmitted therethrough.

The detector arrangement 136 comprises an ionization chamber shell 138 that is partitioned off by a partition 140 to form two ionization chamber detectors 142 and 144. The x rays received from the paper 132 enter the first detector 142 through a window 146 that may comprise a ten to twenty-mil (0.25–0.5 mm) thickness of sheet beryllium that permits the chamber 142 to be adequately pressurized but is substantially transparent to the soft x rays. The dashed line 162 indicates the position of an optional filter that may be used as hereinafter described to help shape the energy spectrum of the x rays entering the chamber 142. The thickness of the filter 162 is shown greatly exaggerated since the actual thickness is typically only a few micrometers ($\mu$m).

The ionization current is collected by an electrode 148 that typically comprises about a five-mil (0.13 mm) thick sheet of beryllium in an aluminum frame. The partition 140 is also typically made of a beryllium sheet, of perhaps five to ten mils (0.13–0.25 mm) thickness, to enable the two detectors to contain different gases at different pressures if appropriate. Hence the first detector detects a portion of the x rays received from the paper 132 to produce a first detector response, and transmits a second portion of the received rays through electrode 148 and partition 140 to the second detector, or ionization chamber 144. The dashed line 150 indicates the location of a filter that is typically used as hereinafter described to help shape the spectrum of the x rays entering the second detector 144. The ionization current in the second detector 144 is collected by an electrode 152. Electrode 152 has a substantial thickness, and chamber 144 is designed to extract as much ionization current as possible from the x rays entering it.

The ionization currents collected from the first and second detectors are amplified by respective high impedance operational amplifiers 154 and 156 to produce originating responses in the form of robust signals at 158 and 160 respectively. These robust signals may be sampled at appropriate times by a digital computer 14a which controls a gating system 80a and an analog to digital converter 82a in a manner similar to that described in connection with FIG. 1. The sampled data may then be handled by the computer as originating responses $S_{M1}$ and $S_{M2}$ (or $S_{M2}$ and $S_{M3}$, or $S_{M1}$ and $S_{M3}$) in two separate channels as previously described in connection with FIG. 3, with the information being used eventually in a calculation of ash content as at 130.

Because of the relative simplicity of th data processing operations outlined in FIG. 3, these operations can, if desired, be performed by conventional analog computer elements.

Depending on the specific construction of the apparatus of FIG. 4, there are a number of options available for carrying out the invention. According to one group of options, the components of a binary ash constituent can be measured. As an example, the measurement of an ash constituent consisting essentially of clay and titanium dioxide will be considered first. In these embodiments, the filter 162 is omitted. The voltage on the x-ray tube in source unit 134 is adjusted as explained in the first article of Cho and Utt, supra, to achieve the crossover point 42 (at voltage $V_2$) so that when the signal 158 (FIG. 4) from the first ionization chamber 142, represented as $S_{M2}$ (FIG. 3) is processed as in FIG. 3, the processed signal $S_2$ is constituted as $$S_2 = C + T \tag{7}$$

where as previously defined C represents the response to clay and T represents the response to TiO$_2$.

Inherently the signal 160 from the second ionization chamber 144 that becomes $S_{M3}$ and eventually $S_3$ in FIG. 3 will not be constituted the same as in Equation (7) because more of the softer x rays than the harder x rays will be absorbed in passing through the first ionization chamber 142, thus "hardening" the spectrum of the rays entering chamber 144. In order to achieve more contrast between the responses to clay and TiO$_2$ in chamber 144, this hardening process can be enhanced if necessary by a filter of aluminum, for example, a few micrometers thick, at 150. The signal $S_3$ will be constituted as $$S_3 = C + A_1 T \tag{8}$$

and Equations (7) and (8) have the simple solution $T = (S_3 - S_2)/(A_1 - 1)$ and $C = S_2 - T$.

Instead of using the enhanced x-ray hardening expendient to obtain greater contrast between the clay and TiO$_2$ responses in chamber 144, a titanium filter on the order of about 5–10 μm thick can be used at 150. The titanium filter will selectively remove most of the rays having energies above the titanium K-edge, thus obtaining from chamber 144 a response constituted as $$S_3 = C + A_2 T \tag{9}$$

Here the constant $A_2$ has a value close to ½ as appears from FIG. 2, since at energies below the titanium K-edge the absorption coefficient of TiO$_2$ is about half that of the clay. Equations (7) and (9) are solved for $T = (S_2 - S_3)/(1 - A_2)$ close to $T = 2(S_2 - S_3)$ and $C = S_2 - T$.

The selection of the x ray energy to achieve the crossover point 42 has several advantages including the computational advantage of making the response $S_2$ of the one channel to the titanium dioxide component the same as its response to the clay component, as exemplified by Equation (7). This is in addition to the advantage resulting from the normalization which makes both channel responses $S_2$ and $S_3$ the same to the clay component. This energy selection, however, is not absolutely essential to permit the computation of the ash components. For example, if the titanium filter is used at 150, without exact energy selection, Equation (7) becomes $$S_2 = C + A_3 T \tag{10}$$

and the second detector produces the same response as in Equation (9). Equations (9) and (10) are solved for $T = (S_3 - S_2)/(A_3 - A_2)$ and $C = S_2 - A_3 T$.

If neither the titanium filter at 150 nor exact energy selection is used, the two channel responses are constituted as $$S_2 = C + A_4 T \tag{11}$$

and $$S_3 = C + A_5 T \tag{12}$$

which can be solved for $T = (S_2 - S_3)/(A_4 - A_5)$ and $C = S_2 - A_4 T$.

The foregoing examples of the application of the apparatus of FIG. 4 have illustrated its use for measuring the components of only one binary ash constituent in paper, specifically a mixture of clay and TiO$_2$. The application of the same apparatus to other binary mixtures such as a mixture of clay and chalk or a mixture of chalk and TiO$_2$ can be accomplished in a similar manner. If a clay and chalk mixture is to be analyzed using a "softening" technique to achieve a contrasting response from the second detector 144, the filter 150 may comprise a few micrometers of tin to selectively remove the x rays having energies above the K-edge of calcium, since no technique is presently known for constructing a practical calcium filter to the required specifications. The characteristics of a tin filter are more fully discussed and illustrated hereinafter.

Next to be considered are the options available according to the invention for measuring the total ash constituent in paper that may contain a binary or tertiary mixture of ash-forming components, for example, any one, any two or all three of the clay, chalk and TiO$_2$ components.

As noted above, the commercial gauge of the Utt and Cho articles, supra, has been able to measure the total ash in paper that may contain any mixture of clay and TiO$_2$ by directing into the paper a beam of x rays whose spectrum is so selected that about 15% of the x-ray intensity lies above the K-edge energy for titanium, with the remaining 85% or so lying below the K-edge, thus achieving the crossover point 42 of FIG. 2 and making the measurement with a single detector in a single channel instrument. Similarly any mixture of clay and chalk could be measured by selecting a spectrum such that about 40% of the x-ray intensity lies above the K-edge for calcium, thus achieving the crossover point 40. However, up to now it has been considered impossible to produce an x-ray spectrum that allows a similar total ash measurement in paper that may contain any mixture of clay, chalk and TiO$_2$.

Figure 7:
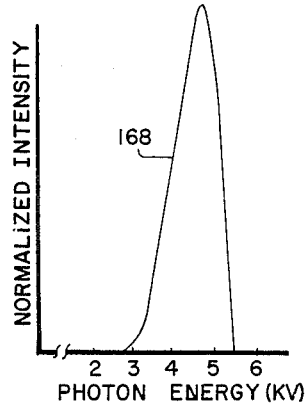
FIG. 7 is a graph showing the spectrum of x rays produced by the x-ray source unit of FIG. 6.
Figure 5:
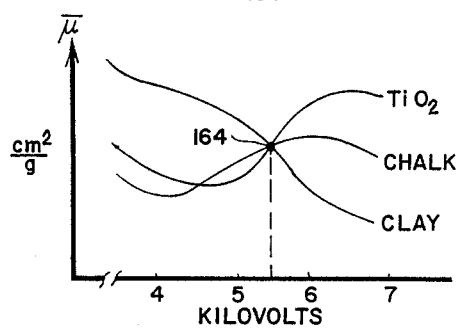
FIG. 5 is similar to FIG. 2, but relating to spectra of x rays that have been shaped so that all three coefficients are equalized for one value of the applied voltage.

Nevertheless, according to this invention it has now been found possible to obtain average effective absorption coefficients that are equal for clay, chalk and TiO$_2$ as shown at point 164 in FIG. 5. To achieve this result, an x-ray source unit 166 (FIG. 6) contains an x-ray tube energized at around 5½ kilovolts to produce a beam of x rays having an energy spectrum 168 as shown in FIG. 7, including the K-edge energy for titanium at 4.966 kev. These x rays are filtered by a filter 170 before they impinge on the paper 172 being measured. An ionization chamber detector 174 receives the rays from the paper.

The filter 170 is designed to selectively absorb x rays having energies between the K-edge energies for calcium and titanium. This particular selectivity is characteristic of L-edge absorption in tin. The tin, if applied as a coating, for example, by vapor deposition on a beryllium window, may have a thickness of about four to eight micrometers (4–8 μm), or if distributed in a matrix, for example, by ion bombardment, should form a weight per unit area of tin equivalent to a tin thickness of about 4–8 μm.

For paper with a nominal basis weight of one hundred grams per square meter (100 g/m²) and a nominal composition including about 10% total ash, a computer model indicates that the thickness of the tin filter 170 should be about 6.6 μm. Without the paper 172 in place, the rays detected by the detector 174 would have the energy distribution shown in FIG. 8. Here the spectrum 176 is normalized to the intensity of the original spectrum 168 of FIG. 7. Actually the tin filter attenuates the rays by a factor of about twenty, so that the x-ray source unit 166 must produce a much more intense beam of x rays than that used in the commercial gauge of the Utt and Cho article supra.

Figure 8:
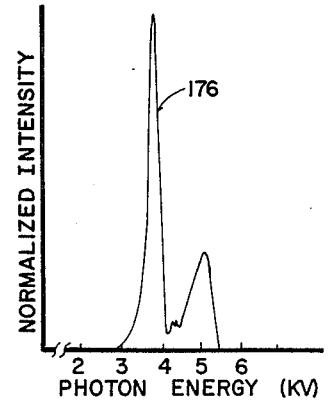
FIG. 8 is a graph showing a normalized spectrum produced by reshaping the spectrum of FIG. 7.

The signal provided by detector 174 is amplified at 176, converted to a digital signal at 178 and utilized by a computer 180 to produce a response as on a line 182 that is appropriately used by a display, recording and/or control device 184 in a manner similar to that described in connection with FIG. 1. Because of the energy selection and the effect of the filter 170 as shown by FIG. 8, the response at 182 is a response to a spectrum of the rays received by the detector system wherein the intensities are so distributed as a function of energy that the average effective absorption coefficients for the clay, the chalk and the $TiO_2$ are substantially equalized as at point 164 in FIG. 5.

A generally similar method and apparatus can be used to measure other traveling products exhibiting variations in the vicinity of a nominal mass per unit area, mass per unit length or mass per unit volume, and in the vicinity of a nominal composition including a constituent of interest made up of any or all of three components formed from distinctive chemical elements, at least two of which have absorption edges in neighboring regions of the x-ray spectrum.

Figure 6:
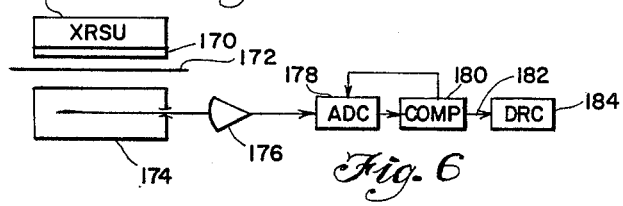
FIG. 6 is a schematic diagram of a single channel x-ray apparatus for measuring the total ash constituent in paper containing a tertiary mixture of ashforming components.

In the paper ash measurement embodiment as illustrated in FIG. 6, with the use of energy selection and the choice of a proper thickness for the tin filter 170 equal average effective absorption coefficients as illustrated in FIG. 5 can be achieved for a selected nominal basis weight and nominal composition. However, once the parameters have been selected, if the basis weight or the composition of the paper being measured becomes greatly different from the nominal basis weight and composition, as the difference increases progressively larger errors will occur. This is because the paper itself acts as a filter that produces some reshaping of the x ray energy spectrum 168 (FIG. 7) produced by the x ray source unit 166.

Accordingly where a substantially wide range of variations in the measured material are to be encountered, or where accurate "tuning" of the gauge parameters cannot be achieved in the first instance, the double-deck detector arrangement of FIG. 4 can be used with the addition of a filter such as the tin filter, in position 162 for example. In this apparatus the second detector is used to correct the response of the one detector for the effects of imperfect geometric compensation for variations in the amount of one component such as the chalk component of paper ash, for example. In this case the responses $S_2$ and $S_3$ may be constituted by $$S_2 = C + T + (1-\delta)H \tag{13}$$

$$S_3 = C + A_6 T + BH \tag{14}$$

Here $\delta$ represents the residual error caused by the lack of fine tuning for chalk, due, for example, to the use of an incorrect thickness of tin for the filter 162.

$\delta$, $A_6$ and $B$ (whose exact values can be determined eventually in calibration) are design constants and are made to satisfy the conditions:

$$\left. \begin{array}{l} |\delta| < 0.1 \\ 1.5 > A_6 > 0.5 \\ 2 > B > 1.5 \end{array} \right\} \tag{15}$$

It is to be noted that $\delta$ can be either positive or negative.

In order to achieve conditions (15), in addition to the selection of materials for filters 150 and 162 there is a choice of the composition and pressure of the filling gas or gases for ionization chambers 138 and 144. In the case of the paper ash analyzer, it is to be noted that xenon has significant L-edges in the 4.7 to 5.4 kev area, krypton has no significant absorption edges in the region of interest, and argon has a K-edge at 3.2 kev. It is expected that argon will generally be used in chamber 138 to increase the amplitude of the signal current from chamber 144. The x-ray tube high voltage is the final tuning parameter to make some adjustment for the effect of manufacturing tolerances.

The solution of Equations (13) and (14) for the total ash content $A_t$ yields $$A_t = \frac{(B-1)S_2}{B-1-\delta} - \frac{\delta S_3}{B-1-\delta} - \frac{\delta(A_6-1)T}{B-1-\delta} \tag{16}$$

Although the measured value of $A_t$ is here dependent on the unknown $TiO_2$ content $T$, it is seen that the second and third terms are only small correcting terms. Since $|\delta| < 0.1$ and $(A_6-1) < 0.5$, the error due to neglecting the third term is less than 1/20 of the actual $TiO_2$ content. Moreover because of its relatively high cost the $TiO_2$ content in a tertiary mixture will not exceed 5%. Thus the error due to neglecting the third term will be less than 0.25%. Hence the total ash is computed from $$A_t = \{(B-1)S_2 - \delta S_3\}/\{B-1-\delta\} \tag{17}$$

If the range of $TiO_2$ content is known, some additional improvement can be made by using $$A_t = \{(B-1)S_2 - \delta S_3 - \tfrac{1}{2}\delta(A_6-1)T_{max}\}/\{B-1-\delta\} \tag{18}$$

where $T_{max}$ represents the maximum expected TiO$_2$ content.

Instead of setting up the conditions (15) it is also possible to set up an alternate set of conditions $$\left.\begin{array}{l} |\delta| < 0.4 \\ |A_6 - 1| < 0.1 \\ 1.5 < B < 2.0 \end{array}\right\} \quad (19)$$

Whereas conditions (15) may require a substantial thickness of tin in filter position 162 together with a hardening filter in filter position 150, conditions (19) may be achieved for example with a considerably thinner thin filter but with an appropriate thickness of titanium in filter position 150. It is to be noted from Equation (16) that Equation (17) will be exact if $A_6=1$ regardless of the value of $\delta$.

Equation (17) is also applicable for the total ash measurement of binary mixtures. It is exact for a clay and chalk mixture, and can be made exact by setting $\delta=0$ for a clay and TiO$_2$ mixture.

As is known to those skilled in the art, multicomponent ash analyzers for use on line with paper making machines and using x rays, gamma rays and the like are subject to certain sources of errors, which, though minor, are significant and apparently irreducible. Where the ash components must be separately measured or calculated and added to obtain total ash, one must accept the fact that in a tertiary ash measurement, for example, the magnitude of the irreducible error may be tripled under certain conditions. This particular problem obviously does not exist with the method and apparatus of FIG. 6, because only a single measurement is involved. It can be seen that the problem is effectively avoided also when the method and apparatus of FIG. 4 is used to measure total ash as by implementing one of equations (16)–(18). Although this is a two-channel arrangement, it uses essentially only one measurement, with the addition of a minor correction term.

While the "double-deck" detector arrangement is important according to some aspects of the invention because of its common mode error rejection characteristics, in some cases two (or more) entirely separate detectors can be used satisfactorily in a pluralchannel arrangement.

While the illustrated arrangement of FIG. 1 utilizes high voltage switching with a single x-ray tube, other devices can be used for shifting the x-ray beam energy between plural spectra. For example, plural x-ray tubes operating continuously at different fixed voltages can be used, and their x-ray beams can be directed separately and sequentially into the material by a rotating, x-ray opaque chopper wheel arrangement.

It is thus apparent that while the invention has been described and illustrated in the form of particular procedures and particular apparatus, the showing and description are illustrative only and not restrictive, since many other changes and modifications can obviously be made without departing from the spirit and scope of the invention.

What is claimed is:

1. A method adapted for determining a constitutent or component of a traveling product that is continuously formed from materials having components of different atomic numbers, comprising directing into the product a beam of x rays having energies including an absorption edge energy for at least one of the components, receiving x rays from the product and responding to the received rays to produce a first channel response and a second channel response wherein at least one of the two channel responses is normalized, the two channel responses being responsive to two different energy spectra in a manner such that after normalization both channel responses are substantially the same to one component although different to the other component, at least one of the energy spectra being selected to produce effective absorption coefficients that are equal in the one channel for the one component and the other component, and thereby to make the response of the one channel to the other component substantially the same as its response to the one component, and responding to the first and second channel responses to produce a resultant response indicative of the content of the constitutent or component in the product.

2. A method adapted for determining a constituent or component of a traveling product that is continuously formed from materials having components of different atomic numbers, comprising directing into the product a beam of x rays having energies including an absorption edge energy for at least one of the components, wherein the x-ray energies in the beam are shifted in a repeating sequence between a first energy spectrum and a second energy spectrum, receiving x rays from the product and sequentially responding to the received rays in the first and second energy spectra to produce first and second channel response, the two channel responses being responsive to the two different energy spectra in a manner such that the channel responses are substantially the same to one component and different to another component, at least one of the energy spectra being selected to produce effective absorption coefficients that are equal in the one channel for the one component and the other component, and thereby to make the response of the one channel to the other component substantially the same as its response to the one component, and responding to the first and second channel responses to produce a resultant response indicative of the content of the constituent or component in the product.

3. A method as in claim 2 wherein the sequence includes a third energy spectrum, the method including responding to the third energy spectrum to produce a third channel response.

4. A method as in claim 3 wherein another of the energy spectra is selected so as to make the response of the third channel substantially the same to a third component as it is to either the one component or to the other component.

5. A method adapted for determining a constituent or component of a traveling product that is continuously formed from materials having different atomic numbers, comprising directing into the product a beam of x rays having energies including an absorption edge energy for at least one of the components, the x-ray energy spectrum and a second energy spectrum by applying different high voltages sequentially to an x-ray tube, receiving x rays from the product and responding sequentially to the first and second energy spectra in the received rays to produce a first channel response and a second channel response, the two channel responses being responsive to two different energy spectra in a manner such that the channel responses are substantially the same to one component and different to another component, at least one of the energy spectra being selected to make the response of the one channel to the other component substantially the same as its response to the one component, and responding to the first and second channel responses to produce a resultant response indicative of the content of the constituent or component in the product.

6. A method adapted for determining a constituent or component of a traveling product that is continuously formed from materials having components of different atomic numbers, comprising directing into the product a beam of x rays having energies including an absorption edge energy for at least one of the components, receiving x rays from the product and responding to the received rays with a first detector that detects a portion of the received rays to originate a first channel response and transmits a second portion of the received rays, filtering the rays transmitted by the first detector to reshape their energy spectrum by selectively reducing the relative intensity of those rays having energies above the absorption edge for the one component, detecting the filtered rays to originate a second channel response, the two channel responses being responsive to two different energy spectra in a manner such that the channel responses are substantially the same to one component and different to another component, and responding to the first and second channel responses to produce a resultant response indicative of the content of the constituent or component in the product.

7. A method adapted for determining a constituent or component of a traveling product that is continuously formed from materials having components of different atomic numbers, comprising directing into the product a beam of x rays having energies including an absorption edge energy for at least one of the components, receiving x rays from the product and filtering the received rays to selectively reduce the relative intensity of those rays having energies below the absorption edge energy for the one component but above the absorption edge energy for the other component, detecting the filtered rays with a first detector that detects a portion of the filtered rays to originate a first channel response and transmits a second portion of the filtered rays, detecting the rays transmitted by the first detector to originate a second channel response, the two channel responses being responsive to two different energy spectra in a manner such that the channel responses are substantially the same to one component and different to another component, and responding to the first and second channel responses to produce a resultant response indicative of the content of the constituent or component in the product.

8. A method as in claim 7 wherein the rays transmitted by the first detector are filtered to further reshape their energy spectrum before they are detected to originate the second channel response.

9. A method adapted for determing ash forming material or a component of ash forming material in a traveling sheet of paper being manufactured by a paper making machine, the ash forming materil having components of different atomic numbers and the paper having a variable basis weight and a variable moisture content, the method comprising directing into the paper a beam of x rays having energies including an absorption edge energy for at least one of the components, receiving x rays from the paper and detecting the received rays to produce a first and a second originating response, producing responses to the basis weight and moisture content of the paper, compensatng each of the first and second originating responses according to the basis weight and moisture content responses, deriving from the compensated responses first and second channel responses that are functions of the ash constituent and substantially independent of the basis weight and moisture contents of the paper, the two channel responses being responsive to two different x-ray energy spectra in a manner such that the channel responses are substantially the same to one ash component and different to another ash component, and responding to the first and second channel responses to produce a resultant response indicative of the content of the ash constituent or component in the paper.

10. A method as in claim 9 wherein the ash constituent has at least two components, and wherein at least one of the first and second channel responses is normalized so that after the normalization both responses are substantially the same to one ash component although different to the other component.

11. A method as in claim 10 wherein at least one of the energy spectra is selected to make the response of the one channel to the other ash component substantially the same as its response to the one ash component.

12. A method of measuring a traveling sheet of paper or the like exhibiting variations in the vicinity of a nominal basis weight and a nominal composition including an ash-forming consitutent made up of any or all of the components of clay, chalk and titanium dioxide, comprising the steps of directing into the paper a beam of x rays having energies including the K-edge energy for titanium, receiving x rays from the paper and producing a response to a spectrum of the received rays wherein their intensities are so distributed as a function of energy that the average effective absorption coeficients for the clay, the chalk and the titanium dioxide are substantially equalized for the nominal basis weight and composition of the paper, the response being indicative of the amount of the ash-forming constituent in the paper and comparatively unaffected by the relative amounts of the clay, chalk and titanium dioxide therein.

13. A method as in claim 12 wherein the beam of x rays directed into the paper is produced by an x-ray source unit including an x-ray tube energized at around 5½ kilovolts.

14. A method as in claim 13 wherein the spectrum is formed by passing the x rays through a filter that selectively absorbs rays through a filter that selectively absorbs rays having energies between the K-edge energies for calcium and titanium.

15. A method as in claim 14 wherein the filter comprises a weight per unit area of tin equivalent to a tin thickness of about four to eight micrometers.

16. A method of measuring a traveling product exhibitng variations in the vicinity of nominal mass per unit area, length or volume, and in the vicinity of a nominal composition including a constituent of interest made up of any or all of three components respectively formed from distinctive chemical elements, at least two of which have absorption edges in neighboring regions of the x-ray spectrum, comprising the steps of
    directing into the product a beam of x rays having energies including the highest significant absorption edge energy for the respective elements of the components, and
    receiving x rays from the product and producing a response to a detected spectrum of the received rays wherein their intensities are so distributed as a fuction of energy that the average effective absorption coefficientes for the three components are substantially equalized for the nominal mass per unit area, length of volume and the nominal composition of the product, the response being indicative of the amount of the constituent of interest in the product and comparatively unaffected by the relative amounts of the three components therein.

17. Apparatus adapted for determining a consitituent or component of a traveling product that is continuously formed from material having components of different atomic numbers, comprising
    means for directing into the product a beam of x rays having energies including an absorption edge energy for at least one of the components,
    means for receiving x rays from the product and for responding to the received rays to produce a first channel response and a second channel response, the two channel respones being responsive to two different energy spectra,
    means for normalizing at least one of the two channel respones so that after the normalization both channel respones are responsive to the two different energy spectra in a manner such that both channel respones are substantially the same to one component although different to the other component,
    at least one of the enrgy spectra being selected to produce effective absorption coefficients that are equal in the one channel for the one component and the other component, and thereby to make the response of the one channel to the other component substantially the same as its response to the one component, and
    means for responding to the first and second channel respones to produce a resultant response indicative of the content of the constituent or component in the product.

18. Apparatus adapted for determining a constituent or component of a traveling product that is continuously formed from materials having components of different atomic numbers, comprising
    means for directing into the product a beam of x rays having energies including an absorption edge energy for at least one of the components,
    means for receiving x rays from the product and for responding to the received rays to produce a first channel response and a second channel response, the two channel responses being responsive to two different energy spectra in a manner such that the channel responses are substantially the same to one component and different to another component,
    means for shifting the x-ray energies in the beam in a repeating sequence between a first energy spectrum and a second energy spectrum, and means for sequentially responding to the first and second energy spectra to produce the first and second channel responses,
    at least one of the energy spectra being selected to produce effective absorption coefficients that are equal in the one channel for the one component and the other component, and thereby to make the response of the one channel to the other component substantially the same as its response to the one component, and
    means for responding to the first and second channel responses to produce a resultant response indicative of the content of the constituent or component in the product.

19. Apparatus as in claim 18 wherein the repeating sequence includes a third energy spectrum, the apparatus including means for responding to the third energy spectrum to produce a third channel reponse.

20. Apparatus as in claim 19 wherein another of the energy spectra is selected so as to make the response of the third channel substantially the same to a third component as it is to either the one component or to the other component.

21. Apparatus adapted for determining a constituent or component of a traveling product that is continuously formed from materials having components of different atomic numbers, comprising
    means for directing into the product a beam of x rays having energies including an absorption edge energy for at least one of the components,
    means for shifting the x-ray energies in the beam in a repeating sequence between a first energy spectrum and a second energy spectrum, the x-ray energy shifting means comprising means for applying different high voltages sequentially to an x-ray tube,
    means for receiving x rays from the product and for responding sequentially to the first and second energy spectra in the received rays to produce a first channel response and a second channel response, the two channel responses being responsive to two different energy spectra in a manner such that the channel responses are substantially the same to one component and different to another component,
    at least one of the energy spectra being selected to make the response of the one channel to the other component substantially the same as its response to the one component, and
    means for responding to the first and second channel responses to produce a resultant response indicative of the content of the constituent or component in the product.

22. Apparatus adapted for determining a constituent or component of a traveling product that is continuously formed from materials having components of different atomic numbers, comprising means for directing into the product a beam of x rays having energies including an absorption edge energy for at least one of the components, means for receiving x rays from the product comprising a first detector means that detects a portion of the received rays to originate a first channel response and transmits a second portion of the received rays, means for filtering the rays transmitted by the first detector means to reshape their energy spectrum by selectively reducing the relative intensity of those rays having energies above the absorption edge energy for the one component, a second detector means for detecting the filtered rays to originate a second channel response, the two channel responses being responsive to two different energy spectra in a manner such that the channel responses are substantially the same to one component and different to another component, and means for responding to the first and second channel responses to produce a resultant response indicative of the content of the constituent or component in the product.

23. Apparatus adapted for determining a constituent or component of a traveling product that is continuously formed from materials having components of different atomic numbers, comprising means for directing into the product a beam of x rays having energies including an absorption edge energy for at least one of the components, means for receiving x rays from the product and for filtering the received rays to selectively reduce the relative intensity of those rays having energies below the absorption edge energy for the one component but abot the absorption edge energy for the other component, a first detector means that detects a portion of the filtered rays to originate a first channel response and transmit a second portion of the filtered rays, and a second detector means for detecting the rays transmitted by the first detector means to originate a second channel response, the two channel responses being responsive to two different energy spectra in a manner such that the channel responses are substantially the same to one component and different to another component, and means for responding to the first and second channel responses to produce a resultant response indicative of the content of the constituent or component in the product.

24. Apparatus as in claim 23 comprising means for filtering the rays transmitted by the first detector means to further reshape their energy spectrum before they are detected to originate the second channel response.

25. Apparatus adapted for determining ash forming material or a component of ash forming material in a traveling sheet of paper being manufactured by a paper making machine, the ash forming material having components of different atomic numbers and the paper having a variable basis weight and a variable moisture content, the apparatus comprising means for directing into the paper a beam of x rays having energies including an absorption edge energy for at least one of the components, means for receiving x rays from the paper and for detecting the received rays to produce a first and a second originating resonse, means for producing responses to the basis weight and moisture content of the paper, means for compensating each of the first and second originating responses according to the basis weight and moisture content responses, means for deriving from the compensated responses first and second channel responses that are functions of the ash constituent and substantially independent of the basis weight and moisture contents of the paper, the two channel responses being response to two different x-ray energy spectra in a manner such that the channel responses are substantially the same to one ash component and different to another ash component, and means for responding to the first and second channel responses to produce a resultant response indicative of the content of the ash constituent or component in the paper.

26. Apparatus as in claim 25 wherein the ash constituent has at least two components, comprising means for normalizing at least one of the first and second channel responses so that after the normalization both responses are substantially the same to one ash component although different to the other component.

27. Apparatus as in claim 26 wherein at least one of the energy spectra is selected to make the response of the one channel to the other ash component substantially the same as its response to the one ash component.

28. Apparatus for measuring a traveling sheet of paper or the like exhibiting variations in the vicinity of a nominal basis weight and a nominal composition including an ash-forming constituent made up of any or all of the components of clay, chalk and titanium dioxide, comprising means for directing into the paper a beam of x rays having energies including the K-edge energy for titanium, means for receiving x rays from the paper and for producing a response to a spectrum of the received rays wherein their intensities are so distributed as a function of energy that the average effective absorption coefficients for the clay, the chalk and the titanium dioxide are substantially equalized for the nominal basis weight and composition of the paper, the response being indicative of the amount of the ash-forming constituent in the paper and comparatively unaffected by the relative amounts of the clay, chalk and titanium dioxide therein.

29. Apparatus as in claim 28 wherein the means for directing the beam of x rays into the paper comprises an x-ray source unit including an x-ray energized at around $5\frac{1}{2}$ kilovolts.

30. Apparatus as in claim 29 wherein the spectrum is formed by passing the x rays through a filter that selectively absorbs rays having energies between the K-edge energies for calcium and titanium.

31. Apparatus as in claim 30 wherein the filter comprises a weight per unit area of tin equivalent to a tin thickness of about four to eight micrometers.

32. Apparatus for measuring a traveling product exhibiting variations in the vicinity of a nominal mass per unit area, length or volume, and in the vicinity of a nominal composition including a constituent of interest made up of any or all of three components respectively formed from distinctive chemical elements, at least two of which have absorption edges in neighboring regions of the x-ray spectrum, comprising
    means for directing into the product a beam of x rays having energies including the highest significant absorption edge energy for the respective elements of the components, and
    means receiving x rays from the product and for producing a response to a detected spectrum of the received rays wherein their intensities are so distributed as a function of energy that the average effective absorption coefficients for the three components are substantially equalized for the nominal mass per unit area, length or volume and the nominal composition of the product, the response being indicative of the amount of the constituent of interest in the product and comparatively unaffected by the relative amounts of the three components therein.

* * * * *

UNITED STATES PATENT AND TRADEMARK OFFICE
CERTIFICATE OF CORRECTION

PATENT NO. : 4,815,116
DATED : March 21, 1989
INVENTOR(S) : Boong Y. Cho

It is certified that error appears in the above-indentified patent and that said Letters Patent is hereby corrected as shown below:

Column 1, line 57, --titanium dioxide. While this gauge has had substantial-- was omitted before "commercial".
Column 4, line 30, "th" should read --the--.
Column 6, line 10, "inexpesive" should read --inexpensive--; line 25, "attentuation" should read --attenuation--.
Column 7, line 46, "or plastics" should read --of plastics--.
Column 11, line 10, "th" should read --the--.
Column 15, line 16, "thin" should read --tin--.
Column 16, (claim 5) line 68, --energies-- in the beam being shifted in a repeating sequence between a first-- was omitted after "x-ray".
Column 18, (claim 9) line 14, "materil" should read --material--; line 26, "compensatng" should read --compensating--.
Column 18, (claim 12) line 64, "coeficients" should read --coefficients--.
Column 19, (claim 16) lines 15 and 16, "exhibitng" should read --exhibiting--; line 16, --a-- was omitted before "nominal"; line 31, "coefficients" should read --coefficients--; (claim 17) line 48, 51, 52 and 54, "respones" should read --responses--; line 19, "enrgy" should read --energy--.
Column 21, (claim 23) line 40, "abot" should read --above--.

UNITED STATES PATENT AND TRADEMARK OFFICE
CERTIFICATE OF CORRECTION

PATENT NO. : 4,815,116
DATED : March 21, 1989
INVENTOR(S) : Boong Y. Cho

It is certified that error appears in the above-indentified patent and that said Letters Patent is hereby corrected as shown below:

Column 22, (claim 25) line 6, "resonse" should read --response--.

Signed and Sealed this

Seventeenth Day of August, 1993

Attest:

BRUCE LEHMAN

*Attesting Officer*  *Commissioner of Patents and Trademarks*